United States Patent
Chu et al.

(10) Patent No.: US 8,517,735 B2
(45) Date of Patent: Aug. 27, 2013

(54) TRANSLUCENT VENEERING FOR A DENTAL PROSTHESIS FORMED BY A PRESS TO METAL PROCESS

(75) Inventors: Christopher C. Y. Chu, West Windsor, NJ (US); Slawomir Banasiak, Kearny, NJ (US)

(73) Assignee: DENTSPLY International Inc., York, PA (US)

( * ) Notice: Subject to any disclaimer, the term of this patent is extended or adjusted under 35 U.S.C. 154(b) by 428 days.

(21) Appl. No.: 12/459,783

(22) Filed: Jul. 8, 2009

(65) Prior Publication Data

US 2009/0274995 A1 Nov. 5, 2009

Related U.S. Application Data

(63) Continuation of application No. 11/788,600, filed on Apr. 20, 2007, now abandoned.

(51) Int. Cl.
*A61C 13/08* (2006.01)

(52) U.S. Cl.
USPC .......................................................... 433/208

(58) Field of Classification Search
USPC .................................. 433/202.1, 212.1, 222.1
See application file for complete search history.

(56) References Cited

U.S. PATENT DOCUMENTS

| | | | |
|---|---|---|---|
| 4,741,699 A | 5/1988 | Kosmos | |
| 4,828,117 A * | 5/1989 | Panzera et al. | 206/63.5 |
| 5,173,114 A * | 12/1992 | Heurtaux | 106/35 |
| 5,713,994 A * | 2/1998 | Kramer et al. | 106/35 |
| 5,788,498 A | 8/1998 | Wohlwend | |
| 2005/0082702 A1 | 4/2005 | Wennemann | |
| 2007/0196788 A1 | 8/2007 | Chu et al. | |

FOREIGN PATENT DOCUMENTS

| | | |
|---|---|---|
| GB | 1072689 | 6/1967 |
| WO | WO 02/076329 | 10/2002 |
| WO | WO 03/068100 | 8/2003 |
| WO | WO 2006/055800 | 5/2006 |

* cited by examiner

*Primary Examiner* — Sunil K Singh
(74) *Attorney, Agent, or Firm* — David A. Zdurne; Douglas J. Hura; Leana Levin

(57) ABSTRACT

A dental prosthesis, typically formed in a press to metal process, includes application of a porcelain composition sufficient to form a veneer on a dental prosthesis supporting metal structure, the composition having an integrated tooth-like translucency providing an aesthetic appearance. The composition is formed of a dentin frit and an enamel frit, typically sintered into a desired ingot shape including an amount of composition sufficient to veneer the prosthesis. The porcelain composition is a component of a kit that includes opaquers, other porcelains and stains useful in finishing to provide an aesthetic prosthesis.

19 Claims, 1 Drawing Sheet

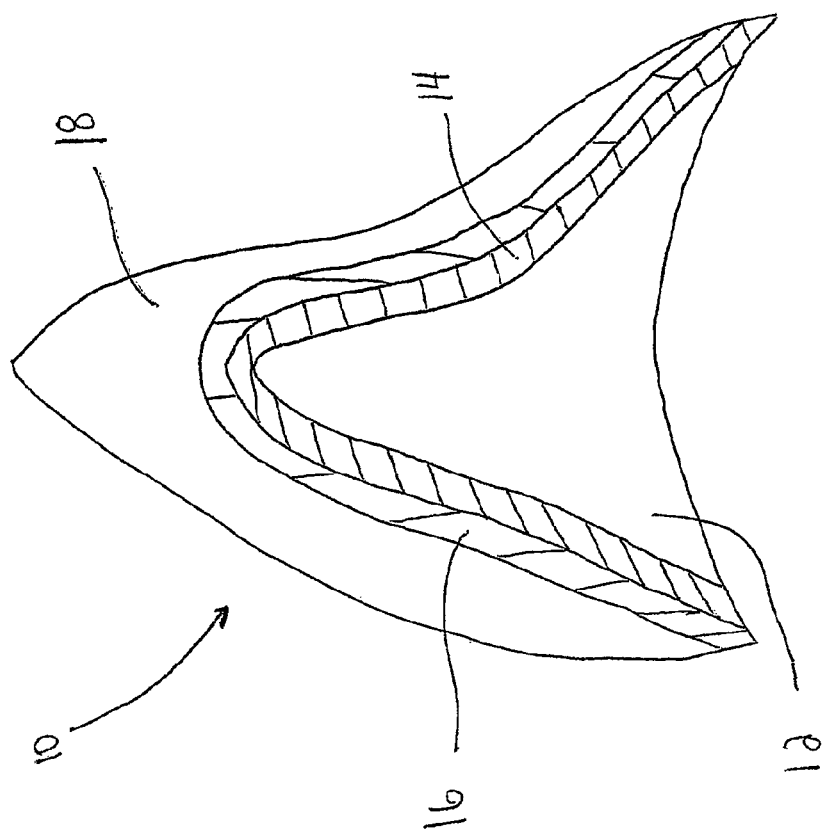

TRANSLUCENT VENEERING FOR A DENTAL PROSTHESIS FORMED BY A PRESS TO METAL PROCESS

RELATED APPLICATIONS

This application is a continuation of application claims the benefit of and priority to U.S. patent application Ser. No. 11/788,600, filed on Apr. 20, 2007, now abandoned, which is herein incorporated by reference for all purposes.

FIELD OF THE INVENTION

The invention relates to dental prostheses comprising porcelain fused to a metal supporting structure or coping. Particularly, the invention relates to prostheses made by pressing a heated ceramic material into a mold onto said coping, wherein the mold is typically made by the lost wax process.

BACKGROUND OF THE INVENTION

A majority of crown and bridge restorations of teeth continue to be porcelain fused to a metal supporting structure or coping that provides strength for the prosthesis. While "all-ceramic" prostheses are of increasing importance, porcelain fused to metal (PFM) remains cost effective and provides satisfactory aesthetics.

Since the metal substructures used in these restorations are not naturally tooth colored, esthetic veneering porcelains are applied that mimic the color and form of natural teeth. The veneering process plays a critical role in providing a satisfactory restoration. Typically the process of making a PFM restoration requires an opaque layer for masking the metal coping; a dentin layer that simulates the color of the tooth dentin; and an enamel layer that simulates the transparency and neutral colors of the tooth enamel. Other materials such as stains are typically used to achieve aesthetic effects.

Each layer is typically applied by hand, first requiring mixing of selected porcelain powders and liquids. The result is subject to variability and depends upon careful work of a skilled ceramist. Achieving consistent, aesthetic results is time consuming and adds significant cost to the final product, as well as requiring people who have a scarce skill and necessary experience.

In a continuing drive to simplify processes and reduce labor costs, methods have been developed to replace the multi-stage porcelain veneering process by a process in which the veneer material is pressed onto the metal support. However, a remaining difficulty has been that the initial pressing must still often be followed by a hand layering with enamel porcelain, particularly to develop incisal edge translucency.

SUMMARY OF THE INVENTION

It is an object of the present invention to provide porcelain materials and processing methods wherein skilled, intensive, and costly hand layering is further reduced.

The invention is a dental prosthesis that includes a metal coping for supporting said prosthesis on tooth surfaces to be repaired. The metal coping is provided with an opaque layer that covers surfaces of the coping that would interfere with achieving an acceptable tooth-like appearance of the finished PFM. The opaque layer may be formed from a mixture of frits in powder or paste form and applied by spraying, a slurry dip, electrodeposit, or other forms or methods known to those skilled in the art. A porcelain layer, having an optimized, integrated translucency that blends dentin and enamel shades is fused to said opaqued surface by pressing the porcelain material onto said coping contained in a mold at fusing temperatures. The result is a strong and tough dental crown or bridge substructure that is veneered with porcelain having an integrated transparency, blending dentin and enamel character, such that further hand layering processes are eliminated or greatly reduced.

BRIEF DESCRIPTION OF THE DRAWINGS

FIG. 1. is a cross-sectional view of a dental prosthesis embodying concepts of the present invention.

DESCRIPTION OF THE PREFERRED EMBODIMENTS

The invention comprises a dental prosthesis, formed of elements, which may be supplied as components of a kit, that provide a porcelain fused to metal (PFM) restoration, using a pressing process to apply a finished surface instead of conventional hand layering of veneering porcelain. The veneering materials of the invention are designed for forming fixed prosthodontics devices that include both anterior and posterior crowns and bridges. Components of the kit, include principally: (1) dentin/enamel ingots having an integrated tooth-like translucency; and (2) opaquing porcelains, in both powder and paste forms, for covering metal coping surfaces that would otherwise be visible through the porcelain veneer. In addition, the kit may include enamel effect porcelains and glaze/stain porcelains for finishing the prosthesis, as necessary.

The veneering kit of the invention is intended for application to a wide range of supporting structure or coping alloys. For example, two commercially available alloys are non-precious NCM Alpha and Advantage, both manufactured by Austenal, formed into a coping by conventional casting techniques, well known to those skilled in the dental arts. The invention may particularly be utilized with conventional PFM alloys, for example, having coefficients of thermal expansion (CTE) of about 14.0 μ/m/K at 500° C. As necessary, the components may be engineered by blending compositions and adjusting their expansion properties to meet the needs of a particular alloy. In general however, the invention may be utilized with current alloys without the need for a new and specialized alloy set.

The press to metal process for making PFM restorations is well known in the art. The invention and its components are readily adapted to the pressing process, providing a significantly improved efficiency to the medium pressure injection molding process.

In the press to metal process, a metal coping is placed in a mold. The coping is then coated with an opaquing porcelain which may be in powder or paste form, applied by spraying, a slurry dip, electrodeposit or in other forms or methods known to those skilled in the art. The opaquing is followed by wax-up and spruing to form a desired finished prosthesis form. The form is then invested, preferably in an all ceramic investment material, and the wax burned out, forming the prosthesis mold. An appropriate amount of integrated translucency porcelain component of the invention is then pressed into the mold, typically under the conditions shown in Table 1 below. The prosthesis is then divested of the molding material for finishing.

The compositions for utilization in the press to metal process are designed such that the prosthesis produced is directly a desired shade match. Of course, the aesthetics may be modified or improved by the use of small amounts of "enamel effect powders". These are typically applied in small sections at desired areas such as incisal edges, cusps, etc., followed by application of an overglaze or stains, as is well known in the art.

TABLE 1

| | | PRESSING CONDITIONS | | | |
|---|---|---|---|---|---|
| Low temp. | High temp. | Heat rate | High temp. | Pressing time | Pressure* |
| 700° C./1292° F. | 890° C./1634 | 60° C./108° F. | 20 min | 10 min | 4.25 bars |

*for Multimat Touch and Press System, use 2.5 bars

The integrated translucency composition of the invention is preferably utilized in the form of an ingot, preferably composed of a mixture of a dentin frit and a more transparent enamel frit. An example of a preferred frit formula for the ingot, as well as preferred ranges of compositions are listed in Table 2. To make the ingot material into a desired white porcelain, it is preferable to add 0.05% of antimony oxide ($Sb_2O_3$) and a fluorescing agent. The ingots are formed of the desired frits, typically in an amount of 2-5 grams, typically by pressing into a desired ingot form, pre-sintering at an initial temperature and further sintering at a higher temperature. The chemical compositions of the ingot white porcelain material together with the two raw frits are listed in Table 3.

TABLE 2

| FRIT FORMULATION OF PORCELAIN INGOT MATERIAL | | |
|---|---|---|
| Frit | Dentin Frit (Range) | Enamel Frit (Range) |
| Weight % | 78 (85-70) | 22 (15-30) |

TABLE 3

| CHEMICAL COMPOSITION OF INGOT WHITE PORCELAIN (WT %) | | | |
|---|---|---|---|
| Oxide | Dentin Frit | Enamel Frit | Ingot white (Range) |
| $SiO_2$ | 64.5 | 64.7 | 64.5 (63-66) |
| $Al_2O_3$ | 10.8 | 17.2 | 12.2 (10-14) |
| $Na_2O$ | 8.1 | 2.5 | 6.9 (5-8) |
| $K_2O$ | 9.6 | 13.2 | 10.4 (9-12) |
| $Li_2O$ | — | 2.4 | 0.5 (0-2) |
| CaO | 3.4 | — | 2.6 (1-4 |
| BaO | 1.8 | — | 1.4 (0-3) |
| $Tb_4O_7$ | 1.8 | — | 1.4 (0-3) |
| $Sb_2O_3$ | | | 0.05 (0-1) |
| fluorescing agent | | | 0.05 (0-1) |
| Total | 100 | 100 | 100 |

The coping opaquer, in powder form, comprises mixing two frits with zirconia ($ZrO_2$). Preferred compositions and ranges are shown in Table 4 and the chemical compositions of powder opaques are listed in Table 5.

TABLE 4

| FRIT FORMULATION OF POWDER OPAQUE | | | |
|---|---|---|---|
| Frit | Frit 1 | Frit 2 | Zirconia |
| Weight % | 50 (40-60) | 35 (30-45) | 15 (12-17) |

TABLE 5

| CHEMICAL COMPOSITION OF POWDER OPAQUE (wt %) | | | |
|---|---|---|---|
| Oxide | Frit 1 | Frit 2 | Powder Opaque White (Range) |
| $SiO_2$ | 64.7 | 64.5 | 54.9 (53-56) |
| $Al_2O_3$ | 17.2 | 10.8 | 12.4 (10-14) |
| $Na_2O$ | 2.5 | 7.1 | 3.7 (3-5) |
| $K_2O$ | 13.2 | 8.7 | 9.6 (8-11) |
| $Li_2O$ | 2.4 | — | 1.2 (0-2) |
| CaO | — | 3.4 | 1.2 (0-2) |
| BaO | — | 1.8 | 0.6 (0-1) |
| $CeO_2$ | — | 1.9 | 0.7 (0-1.5) |
| $Tb_4O_7$ | — | 1.8 | 0.7 (0-1.5) |
| $ZrO_2$ | — | — | 15.0 (12-17) |
| Total | 100 | 100 | 100 |

An alternative coping opaquer, in paste form, also comprises two frits: Frit 1 and Frit 3, mixed with zirconia ($ZrO_2$), tin oxide ($SnO_2$), cerium oxide ($CeO_2$), titanium oxide ($TiO_2$), and antimony oxide ($Sb_2O_3$). The frit mixing formula is listed in Table 6 and the chemical composition of paste opaque is listed in Table 7.

TABLE 6

| FRIT FORMULATION OF PASTE OPAQUE | | | | | | | |
|---|---|---|---|---|---|---|---|
| Frit | Frit 1 | Frit 3 | Zirconia | Tin | Cerium | Titanium | Antimony |
| Weight % | 47 (40-50) | 21 (20-30) | 27 (25-35) | 3 (0-4) | 1.5 (1-2) | 0.5 (0-1) | 0.05 (0-1) |

TABLE 7

CHEMICAL COMPOSITION OF PASTE OPAQUE (wt %)

| Oxide | Frit 1 | Frit 3 | Paste Opaque White |
|---|---|---|---|
| $SiO_2$ | 64.7 | 64.5 | 43.28 (42-45) |
| $Al_2O_3$ | 17.2 | 10.8 | 10.19 (8.5-11.5) |
| $Na_2O$ | 2.5 | 8.1 | 2.84 (2-4) |
| $K_2O$ | 13.2 | 9.6 | 8.10 (6-9) |
| $Li_2O$ | 2.4 | — | 1.11 (0.5-2) |
| CaO | — | 3.4 | 0.70 (0.5-2) |
| BaO | — | 1.8 | 0.37 (0-1) |
| $CeO_2$ | — | 1.3 | 1.75 (1-2) |
| $SnO_2$ | — | — | 2.95 (0-4) |
| $TiO_2$ | — | — | 0.49 (0-1) |
| $Sb_2O_3$ | — | 0.5 | 0.15 (0-1) |
| $ZrO_2$ | — | — | 26.59 (25-35) |
| Total | 100 | 100 | 100 |

FIG. 1 illustrates a dental prosthesis employing concepts of the present invention, which include a restoration 10 shown to be mounted in place on a prepared tooth 12. The prosthesis 10 includes a coping 14, which is covered by an opaque layer 16, which in turn is covered by a single porcelain layer 18.

What is claimed is:

1. A dental prosthesis, comprising:
a metal coping for supporting and fitting said prosthesis onto tooth surfaces requiring repair or replacement;
an opaque layer covering surfaces of said coping that would otherwise adversely affect the tooth-like appearance of the finished prosthesis, the opaque layer being in a powder form and being formed from a opaque mixture having:
40 to 60% by weight a first frit;
30 to 45% by weight a second frit, said second frit being different than said first frit; and
$ZrO_2$; and
a single porcelain layer having an integrated tooth-like translucency fused to said opaqued coping surface, said porcelain comprising a blend of dentin and enamel frits, said enamel having more transparency than said dentin, in ratios of 70:30 to 85:15 percent by weight, respectively.

2. The dental prosthesis of claim 1 wherein said opaque layer is applied by spraying, a slurry dip or electrodeposit.

3. The dental prosthesis of claim 1, wherein the blend of the dentin frit and the enamel frit includes:
70 to 85% by weight the dentin frit; and
15 to 30% by weight the enamel frit, the enamel frit being different than the dentin frit.

4. Method of making a porcelain veneered dental prosthesis including a supporting coping, in a hot press furnace having means for injecting a ceramic porcelain material into an investment mold, comprising the steps of:
forming an opaquing ceramic mixture by blending
40 to 60% or by weight a first frit;
20 to 45% by weight a second frit, the second frit being different from the first frit; and
$ZrO_2$;
coating and firing said coping with the opaquing ceramic mixture to form an opaque layer fused to said coping;
investing said dental coping in a mold forming an adjacent cavity for receiving a veneer to be fused to said opaque layer of said coping; and
injecting, under heat and pressure, into said veneer cavity a porcelain ceramic having an integrated tooth-like translucency wherein said porcelain ceramic forms a translucent layer that is fused to said opaque layer of said coping, thereby forming a finished prosthesis having a tooth-like appearance.

5. The method of claim 4 further comprising forming said porcelain ceramic by blending dentin and enamel frits, said enamel frits having more transparency than said dentin frits, in ratios of 70:30 to 85:15 percent by weight, respectively.

6. The dental prosthesis of claim 1, wherein the second frit includes at least two of the following components:
CaO,
BaO,
$CeO_2$, and
$Tb_4O_7$.

7. The dental prosthesis of claim 1, wherein the single porcelain layer further includes $Sb_2O_3$.

8. The method of claim 4, wherein the opaque layer is in powder form.

9. The dental prosthesis of claim 8, wherein the second frit includes at least two of the following components:
CaO,
BaO,
$CeO_2$, and
$Tb_4O_7$.

10. The method of claim 4, wherein the opaque layer is in paste form.

11. The dental prosthesis of claim 10, wherein the second frit includes at least two of the following components:
CaO,
BaO,
$CeO_2$, and
$Sb_2O_3$.

12. The dental prosthesis of claim 4, wherein the porcelain ceramic includes $Sb_2O_3$.

13. The dental prosthesis of claim 4, wherein said opaquing ceramic is applied by spraying, a slurry dip or electrodeposit.

14. The method of claim 4, wherein the blend of the dentin frit and the enamel frit includes:
70 to 85% by weight the dentin frit; and
15 to 30% by weight the enamel frit, the enamel frit being different than the dentin frit.

15. A dental prosthesis, comprising:
a metal coping for supporting and fitting said prosthesis onto tooth surfaces requiring repair or replacement;
an opaque layer covering surfaces of said coping that would otherwise adversely affect the tooth-like appearance of the finished prosthesis; and
a single porcelain layer having an integrated tooth-like translucency fused to said opaqued coping surface, said porcelain layer comprising a blend of dentin and enamel frits, said enamel having more transparency than said dentin, in ratios of 70:30 to 85:15 percent by weight, respectively;
wherein the blend of the dentin frit and the enamel frit includes:
70 to 85% by weight the dentin frit; and
15 to 30% by weight the enamel frit, the enamel frit being different than the dentin frit.

16. The dental prosthesis of claim 15, wherein the opaque layer is in a paste form that includes a mixture of:
40 to 50% by weight a first frit;
20 to 30% by weight a second frit, the second frit being different than the first frit; and
$ZrO_2$.

17. The dental prosthesis of claim 16, wherein the mixture of the opaque layer further includes at least one of the following components:

$SnO_2$, and
$TiO_2$.

18. The dental prosthesis of claim 15, wherein the opaque layer is in a paste form that includes:
$ZrO_2$, and at least one of the following components:
$SnO_2$,
$CeO_2$,
$TiO_2$, and
$Sb_2O_3$.

19. The dental prosthesis of claim 15, wherein said opaque layer is applied by spraying, a slurry dip or electrodeposit.

* * * * *